United States Patent

Leroy et al.

[11] Patent Number: 5,887,481
[45] Date of Patent: Mar. 30, 1999

[54] CATHODE SPUTTERING TARGETS WITH A LOW LEVEL OF PARTICLE EMISSION, PRECURSORS OF THESE TARGETS, AND PROCESSES FOR OBTAINING THEM

[75] Inventors: Michel Leroy, Saint-Egreve; Jean Muller, Voiron, both of France

[73] Assignee: Aluminium Pechiney, Lyons Cedex, France

[21] Appl. No.: 762,415

[22] Filed: Dec. 9, 1996

[30] Foreign Application Priority Data

Feb. 13, 1996 [FR] France .................................. 96 01990

[51] Int. Cl.$^6$ ........................... G01N 33/20; G01N 29/10
[52] U.S. Cl. ................................ 73/866; 73/1.86; 73/627; 204/192.13; 204/298.03
[58] Field of Search .......................... 73/866, 602, 620, 73/627, 628, 629, 631, 646, 1.82, 1.86, 1.01, 183; 204/192.13, 192.33, 298.03, 298.12, 298.13; 324/222, 240, 237, 238, 202; 378/58, 207

[56] References Cited

U.S. PATENT DOCUMENTS

| | | | |
|---|---|---|---|
| 4,366,713 | 1/1983 | Gilmore et al. | 73/618 |
| 4,741,212 | 5/1988 | Rehwald | 73/600 |
| 4,877,505 | 10/1989 | Bergmann | 204/198.12 X |
| 5,160,388 | 11/1992 | Legresy et al. | 204/298.13 X |
| 5,406,850 | 4/1995 | Bouchard et al. | 73/620 |
| 5,584,972 | 12/1996 | Lantsman | 204/192.12 |

OTHER PUBLICATIONS

Patent Abstracts of Japan, vol. 12, No. 443 (p-790), Nov. 22, 1988, JP-A-63-172960, Jul. 16, 1988.

*Primary Examiner*—Thomas P. Noland
*Attorney, Agent, or Firm*—Oblon, Spivak, McClelland, Maier & Neustadt, P.C.

[57] ABSTRACT

A process is provided for ultrasonic testing the internal soundness of cathode sputtering targets including an active part made of very pure aluminum or of very pure aluminum alloy. In particular, this process, after the choice of an ultrasound sensor functioning at an operating frequency greater than 5 MHZ, and preferably between 10 and 50 MHZ, and adjustment of the appropriate measurement sequence, using a target immersed in a liquid and having certain artificial defects simulating the decohesions in the target, consists of taking a count in terms of size and number of the internal decohesions per unit volume and of selecting the targets with a decohesion density of $\leq 0.1$ decohesion larger than 0.1 mm per cm$^3$ of active metal of the targets, and preferably less than 0.1 decohesion larger than 0.04 mm per cm$^3$ of active metal. The process also pertains to selecting precursors of the cathode sputtering targets, containing less than 0.1 internal decohesion larger than 0.04 mm per cm$^3$.

17 Claims, 1 Drawing Sheet

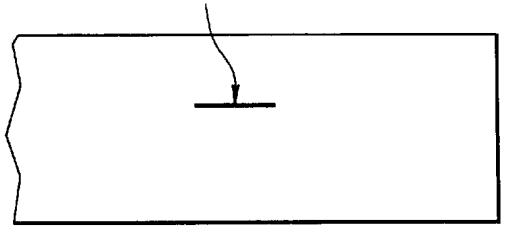
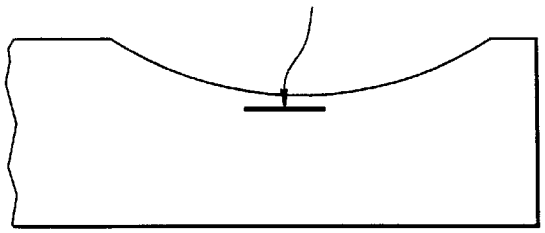
FIG. 1  FIG. 2
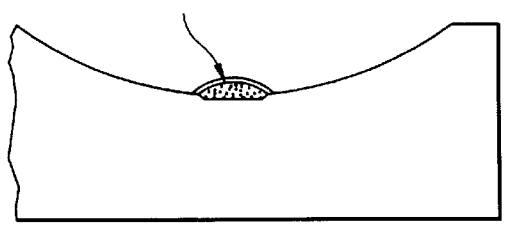
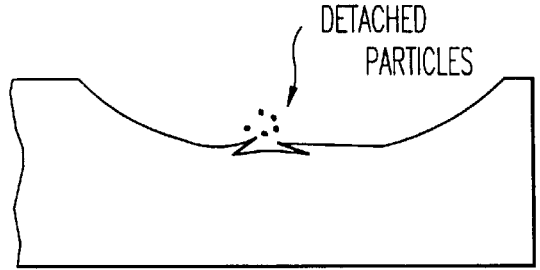
FIG. 3  FIG. 4
FIG. 5

CATHODE SPUTTERING TARGETS WITH A LOW LEVEL OF PARTICLE EMISSION, PRECURSORS OF THESE TARGETS, AND PROCESSES FOR OBTAINING THEM

BACKGROUND OF THE INVENTION

FIELD OF THE INVENTION

The invention pertains to targets or cathodes based on aluminum with a very high degree of purity, which are intended for cathode sputtering on a substrate for manufacturing integrated circuits in particular, as well as to the precursors of these targets or cathodes. In the following, the word "target" also designates the cathodes.

The invention more particularly pertains to processes for the inspection, particularly by ultrasound, of the internal soundness of the targets and of the target precursors, as well as to the selected targets and precursors coming from these processes.

DISCUSSION OF THE BACKGROUND

Cathode sputtering is a deposition technique whose principle is described abundantly in the specialized scientific literature. It allows one to deposit practically all types of materials, refractory or nonrefractory, alloyed or not, conductive or dielectric, on all types of substrates which accept being put under vacuum and slight heating. This deposition technique has been applied extensively in electronics for the coating of semiconductor silicon wafers with an aluminum alloy and the manufacture of integrated circuits. Thus, the manufacture of integrated circuits with a high level of integration, for example, DRAM memories with a capacity greater than 4 MB, requires the deposition of metallic interconnection layers of small thickness (approximately 1 $\mu$m), which are then etched to form extremely fine lines (less than 0.5 $\mu$m in width) allowing individual access to each memory position.

One sees that under these conditions, any defect in the metallization layer, whose size is close to the width of an interconnection line, can lead to a redhibitory defect during the etching operation of the integrated circuit, and lead to the rejection of the integrated circuit.

Among these defects in the metallization layers, which are obtained by cathode sputtering under vacuum using a metallic target, one of the most frequent is the tearing of fine particles from the surface of the target and redeposition of these fine solid or liquid or dust particles on the semiconductor substrate during metallization. The size of this dust or these particles is generally between a few tenths of a micron to a few microns.

In the case of the earlier generations of integrated circuits, whose etching width was several microns, the majority of the particles thus redepositing on the metallized layer of the substrate did not cause any significant etching defects, and the proportion of metallized substrates rejected because of etching defects for this reason could be tolerated.

In contrast, in the case of the current and future generations of ultra-large-scale integrated circuits, for example, the DRAM memories of 16 MB or more, the fineness of etching has been considerably stressed, and the width of the line has been brought to a few tenths of a micron (currently on the order of 0.2–0.5 $\mu$m). Under these conditions, the very fine particles torn from the target and redeposited on the semiconductor substrate have become a major cause for rejection of integrated circuits, and each year, this defect costs the worldwide electronics industry considerable sums of money, greater by several orders of magnitude than the cost of the metallization targets which are used.

It is becoming obvious that the electronics industry has a major stake in eliminating this defect, or at the very least, limiting it, and is a justification for the very extensive research and development efforts on the part of this industry for the purpose of understanding the origin of this defect and remedying it.

These efforts, however, have up to now remained without effect, in spite of the attempts aiming to act on the conditions of preparation of the target, for example, by refinement and homogenization of the sizes of the particles below 0.1 mm according to EP-A-0,466,617 (U.S. Pat. No. 5,160,388). It should also be noted that in this field, nondestructive testing methods, particularly the ultrasonic inspection methods for testing the regularity of the active metallic layer of the target in comparison with a reference layer with an equivalent average particle size, according to U.S. Pat. No. 5,406,850, do not help explain and a fortiori limit this serious problem.

Various hypotheses have been issued as to the origin of the particles redeposited on the substrate in the course of metallization:

A first hypothesis is a two-step mechanism:
In a first step, a part of the metal torn atom by atom from the target is deposited on the walls of the sputtering reactor, or on pieces of equipment contained in this reactor, such as the collimating grid located between the sputtering target and the substrate, and forms a fine deposit there.
In a second step, this deposit is torn again from its support, in the form of fine particles, and is projected onto the semiconductor substrate during metallization.

However, this mechanism, if it exists, can only be completely secondary, because it does not explain a major observation, which is the following:

When one observes a high level of emission and redeposition of particles on several consecutive substrates, it is very often sufficient to change the sputtering target to stop the phenomenon: the emission (and redeposition) of particles is therefore an intrinsic characteristic of the target.

A second hypothesis issued to explain this characteristic effect, connected with an unknown property of the sputtering target, was to suspect the presence of fine inclusions in the metal, such as inclusions of oxides, nitrides, carbides, etc., in the metallic matrix of which the target is composed.

These refractory and electrically nonconductive particles could be electrically charged under the effect of bombardment of the target with argon ions, and could ultimately give rise to the establishment of an electric arc (phenomenon called "arcing"), and then to the melting of the metal surrounding the particle and to its being thrown in the form of multiple micron-sized liquid droplets onto the substrate (phenomenon known as "splashing" or "spattering"), or else to the explosion of the refractory particle under the effect of the accumulated electrostatic charge (phenomenon known as dust application or "dusting").

This hypothesis, which calls for the presence of inclusions whose content can vary from target to target, does explain certain experimentally observed phenomena, and in particular the phenomena of local triggering of an electric arc on the target, during use, which one sometimes observes.

Thus, in one publication, "Effect of thin film oxide inclusions on aluminum target arcing and particulate," presented in Minneapolis in October 1995 to the Annual Congress of the American Vacuum Society, A Leybovich, R. S. Barley, and J. Poole of Tosoh SMD Inc. indicate that large particles of aluminum oxide ($\phi$>1 mm) coming from local electrochemical oxidation of the surface of the target and distributed parallel to this surface can cause "arcing." However, equally extensive defects can be detected by conventional ultrasonic inspection between 1 MHz and 3 MHz and are not normally present in the industrial targets after standardized testing providing for elimination of targets in case of a defect level of 0.7 mm.

This phenomenon is therefore not general: it is a "catastrophic" and destructive phenomenon, which is fortunately not very common, and can only explain an often limited fraction of the emissions of submicron particles observed more commonly, except if the metal used to manufacture the target was particularly dirty and in particular had large quantities of large-sized refractory inclusions present initially in the liquid metal or generated during the casting process, for example more than 5 mg of refractory particles with an average size greater than 30 $\mu$m/kg of metal.

Furthermore, this hypothesis does not explain another experimental observation known to experts in the metallization of integrated circuits, which is that the level of particle emission is a function of the alloy constituting the target, aluminum-silicon-copper alloys (for example, Al+1% Si+0.5% Cu) being the most sensitive, followed by the aluminum-silicon alloys (for example, Al+1% Si), and finally the aluminum-copper alloys with a small copper load (for example, Al+0.5% Cu) being the least sensitive.

No correlation between the chemical composition of the alloy constituting the target and its refractory inclusion content has ever been revealed, and this relationship between the nature of the alloy constituting the target and the level of particle emission has until now remained a mystery.

The applicant has therefore attempted to obtain cathode sputtering targets for the electronics industry which are certain to have very limited particle emission levels, regardless of the aluminum-based alloy used, as well as target precursors, and intermediate products allowing one to obtain them in a reliable and satisfactory manner.

OBJECT OF THE INVENTION

The invention pertains to sputtering targets for the metallization of integrated circuits or of electronic circuits, particularly for applications requiring a very high degree of etching fineness, of which the active part is made of aluminum with a very high degree of purity or of a very pure aluminum alloy, characterized by the fact that they were selected according to a suitable selection process, which advantageously uses a method for testing the internal soundness of the metal, which is nondestructive and sensitive to the internal decohesions, so that the level of rejection of the metallized substrates because of redeposition of solid or liquid particles is less than 5%.

The invention also pertains to a process for testing targets made of aluminum or aluminum alloy which allows one to obtain the targets according to the invention. The process according to the invention is applied particularly to the active part of the targets, that is, the part of the target which is susceptible to removal during cathode sputtering and, more specifically, which is made of aluminum with a high degree of purity or of a very pure aluminum alloy.

The process for testing cathode sputtering targets according to the invention is characterized in that by using a method for testing the internal soundness of the metal which is nondestructive and sensitive to the internal decohesions, one determines the size of the decohesions of the targets to be tested, preferably by comparison with reference targets or with artificial reference defects, for the purpose of calibration, one does a count in terms of size and number of the internal decohesions per unit volume of said targets to be tested, one selects, according to a criterion based on the distribution of the decohesions in terms of size and number, the targets which allow one to reduce the level of rejection of the metallized substrates, because of redeposition of solid or liquid particles, to less than 5%.

The invention also pertains to target precursors which allow one to obtain the targets according to the invention, as well as to a testing process which is also sensitive to the internal decohesions and which allows one to obtain said precursors. Said precursors include in particular the starting billets made of very pure aluminum or very pure aluminum alloy, directly from casting or heat-treated, and the intermediate products such as sections of said billets and target blanks.

The invention in effect contributes a solution to the problem which arises and is based on the unexpected observation that there is a correlation between the level of particle emission and the number and size of defects in the residual metal of the target which are present mainly as flat decohesions which can be measured using a testing method which is sensitive to these decohesions. The presence of decohesions is sometimes associated with small blisters on the surface of the target.

SUMMARY OF THE INVENTION

The sputtering targets for the metallization of integrated circuits or of electronic circuits, of which the active part is made of very pure aluminum or of a very pure aluminum alloy, which have been selected according to the invention, are characterized by the fact that they preferably have a decohesion density of less than or equal to 0.1, decohesion larger than 0.1 mm per cubic centimeter of active metal of the target, and more preferably, less than 0.01 decohesion per cubic centimeter of said metal.

The process for testing cathode sputtering targets according to the invention is characterized by the fact that:

by using a method for testing the internal soundness of the metal which is nondestructive and sensitive to the internal decohesions, one determines the size of the decohesions of the targets to be tested, preferably by comparison with reference targets or artificial reference defects, for the purpose of calibration, one does a count in terms of size and number of the internal decohesions per unit volume of said targets to be tested, one selects, particularly for the applications requiring a very high degree of etching fineness, the targets preferably with a decohesion density of less than or equal to 0.1 decohesion larger than 0.1 mm per cubic centimeter of active metal of the target, and more preferably, less than 0.01 decohesion per cubic centimeter of said metal.

The testing method is chosen from the methods which allow one to determine the size of the decohesions in very pure aluminum or in very pure aluminum alloys, such as the ultrasound methods, the methods based on eddy currents, preferably focused, or the methods using X-rays, preferably focused.

According to a preferred embodiment of the invention, the process uses an ultrasound testing method and is characterized by the fact that:

after having chosen an ultrasound sensor functioning at an operating frequency greater than 5 MHz and preferably between 10 and 50 MHz, and after adjustment of the appropriate measurement sequence indicating the amplitude of the ultrasound echo of an artificial defect of known size, simulating a decohesion in a target immersed in a liquid, as a function of the position of said defect with respect to the surface of the target:

one determines the size of the decohesions of the targets to be tested, by comparison with the amplitude of the ultrasound echo obtained with the artificial defect in a given volume parameterized by the ultrasonic inspection, one does a count in terms of size and number of the internal decohesions per unit volume of said targets to be tested, one selects the targets with a decohesion density of preferably less than or equal to 0.1 decohesion larger than 0.1 mm per cubic centimeter of active metal of the target, and more preferably less than 0.01 decohesion per cubic centimeter of said metal.

Advantageously, the testing method uses, with a sensor or probe adjusted to the operating frequency, a suitable measuring sequence, that is, a transmitter which delivers a pulse whose duration is compatible with the frequency of the sensor and a receiver whose sensitivity is maximum in the frequency band used.

BRIEF DESCRIPTION OF THE DRAWINGS

The preferred embodiments of this invention will be described in detail, with reference to the following figures, wherein:

FIG. 1 is a diagram of a sputtering target.
FIG. 2 is a diagram of a sputtering target.
FIG. 3 is a diagram of a sputtering target.
FIG. 4 is a diagram of a sputtering target.
FIG. 5 is a diagram of a sputtering target.

DETAILED DESCRIPTION OF THE PREFERRED EMBODIMENTS

By attentively observing partially used targets which have given rise to very high levels of particle emission, the applicant curiously observed that several of these targets had, on the surface eroded by the effect of the arc, minuscule blisters (or bubbles) between 0.1 mm and sometimes up to 1 mm in diameter, certain blisters also being open with eroded edges.

By making sections of these blisters, it was proven that the inside of these blisters was empty and that the base of them was roughly flat and parallel to the initial surface of the target. This base sometimes had a few oxide inclusions or precipitates of alloy elements, but this was not a general phenomenon. In effect, it was more frequent in the case of the alloys with small loads of added elements (for example, Al+0.5% Cu), but it was much less general in the case of the more highly loaded alloys (for example, Al+1% Si+0.5% Cu).

By conducting a test with high-frequency ultrasound at more than 5 MHz on the residual metal of these targets, the presence in this metal of flat decohesions parallel to the base surface of the target was detected. The apparent diameter of these decohesions, as judged in reference to the artificial defect, in this case a flat-bottomed hole 0.1 mm in diameter, was between approximately 0.04 and 0.4 mm. The abundance of these defects was variable but was more than one decohesion larger than 0.04 mm per cubic centimeter of inspected metal, and very often more than 0.1 decohesion with a diameter greater than 0.1 mm, per cubic centimeter of inspected metal.

This surprising observation of a correlation between the level of particle emissions, the presence in the residual metal of the target of flat decohesions with dimensions between 0.04 and 0.4 mm, and the presence, on the surface of the used target, of small blisters or craters with a diameter generally greater than 0.1 mm, but sometimes simply greater than 0.04 mm, constitutes the basis of the invention.

The applicant also observed that the rough casting product from which the defective target comes originally has small decohesions such as microporosities, micro shrinkages, or else refractory inclusions, of equivalent size—in order of magnitude—to these defects on targets.

Simply as an attempt at an explanation, it is possible to consider that the mechanism leading to the abundant emission of solid or liquid particles of submicron or micron size by a defective target in the course of use could be the following.

During the transformation into target blanks by forging, pressing, and/or rolling, arbitrarily shaped decohesions are crushed and flattened parallel to the surface of the blank. These decohesions, which constitute a local obstacle to evacuation of the heat introduced in the target by impact of the ion beam intended progressively to liberate the metal atoms constituting the active part of the target, lead to the increasingly rapid heating of the membrane separating the flat decohesion from the surface of the target. This heating of the membrane, which increases in significance as the thickness of the membrane decreases, can then reach a point such that this membrane reaches its melting temperature. Melting would occur when the thickness of the residual membrane would reach approximately $1/1000$ to $1/10$ of the diameter of the decohesion. Several factors, such as the power transmitted to the active part of the target by the ion arc, the thermal or electric conductivity of the alloy used, its metallurgical state, affect by more than one order of magnitude the critical size of the decohesions giving rise to melting of the membrane separating the decohesion responsible for the emission of particles from the eroded surface during use of the target, that is, the critical size of the decohesions responsible for the redeposition of particles could be between 0.01 mm and 1 mm, depending on the precise conditions of operation, but is most often between 0.04 and 0.4 mm under the usual industrial conditions.

An aggravating phenomenon could also be the following, in reference to FIGS. 1 to 5 which represent successive phases of damage to the target. During transformation heat treatments, the hydrogen dissolved in atomic form in the metal and in a supersaturated state diffuses towards these decohesions and is released there in the form of a molecular gas (whose pressure can reach several atmospheres).

At the time of its positioning in the cathode sputtering apparatus, the defective target therefore has flat decohesions parallel to the surface of the target and also filled with molecular hydrogen, according to FIG. 1; these decohesions possibly containing high local concentrations of inclusions or precipitates.

During cathode sputtering, the free surface of the target is progressively eroded until the flat decohesion inside the target is no longer separated from this surface except by a fine membrane of metal, according to FIG. 2.

The aggravating effect of the presence of occluded molecular hydrogen is that under the effect of the pressure difference existing between the hydrogen contained in the decohesion and the vacuum predominating in the cathode sputtering chamber, this fine membrane rises and during sputtering gives rise to a blister or protrusion consisting of a fine membrane of metal separated from the metal mass constituting the rest of the target, according to FIG. 3.

It is then possible to consider that this membrane, separated from it massive support and forming a large protrusion, becomes detached in small solid or liquid fragments during the rest of the cathode sputtering and that these membrane fragments detached from the target become redeposited on the substrate in the course of metallization, according to FIG. 4. These membrane fragments can furthermore be associated with solid particles, such as intermetallic particles or inclusions initially present on the surfaces bordering the decohesion.

Finally, with continuation of the cathode sputtering, the erosion of the surface of the target causes the progressive disappearance of the membrane, according to FIG. 5, and therefore the defect at the origin of the emission of particles.

Several observations support these mechanism proposals:

On the one hand, one very often observes that the deposition of particles on the semiconductor substrate appears suddenly, affects several consecutive substrates, and then disappears.

This could correspond to the time necessary for the membrane, initially several microns or tens of microns thick, to be completely eroded and for the defect to have therefore disappeared.

On the other hand, one observes that the alloys most sensitive to the particle emission phenomenon are also those whose solidification interval (that is to say the difference between the temperature at the beginning of solidification and the temperature at the end of solidification) is the greatest: they are also therefore the alloys which are most sensitive to the formation of microporosities or microshrinkages from contraction at the end of solidification, and with all other conditions equal otherwise (dissolved gas content or inclusion content).

Moreover, on certain defective targets which have given rise to a high level of particle emission, no blister of very small size, less than 0.1 mm in diameter, was detected, whereas there are numerous flat defects less than 0.1 mm in the residual metal of the target, and in particular, numerous defects greater than 0.04 mm.

This could perhaps be explained in the following way:

For a blister to be able to form under the effect of the internal pressure of the hydrogen contained in the flat decohesion, it is necessary for the thickness of the metal membrane separating the decohesion from the surface of the target in the course of erosion, to fall below a critical value which is proportional to the diameter of the decohesion and depends also on the internal hydrogen pressure and on the mechanical strength of the membrane, which is a function of the alloy and the temperature.

For decohesions of very small size (less than 0.1 mm), this critical thickness is very small (approximately 1 to 10 $\mu$m, as an order of magnitude).

Under these conditions and taking into account the heating of the surface of the target under the effect of the ion bombardment, the hydrogen present in the decohesion has the time to diffuse through the metal toward the vacuum of the sputtering chamber before the residual critical thickness allowing for the formation of a blister is reached. This, furthermore, does not modify the heat insulating effect of the decohesion, even of small size, and can cause the melting of the alloy.

The decohesion thus being emptied by diffusion of the hydrogen contained by it through the residual membrane, a blister can no longer form, because the moving force causing its formation (the internal hydrogen pressure) disappears. This potential explanation based on observation implies as a consequence that only the decohesions with a size greater than the critical size, on the order of 0.1 mm for a metal with an ordinary hydrogen content, that is, less than 0.20 ppm and preferably less than 0.10 ppm, can give rise to the formation of blisters in the course of operation, and therefore promote a more significant emission of particles which are then redeposited on the semiconductor substrates. This does not keep such small decohesions, which form a thermal barrier to evacuation of the heat introduced by the ion beam, from being able to bring about local melting, orthogonal to these decohesions, of the alloy forming the active part of the target, and therefore to the projection, on the substrate to be metallized, of redhibitory liquid droplets.

One skilled in the art will understand that the order of magnitude of the critical size of the defects giving rise to emission of particles can vary as a function of the alloy (mechanical strength of the residual membrane), the conditions of deposition (surface temperature of the target, speed of erosion of the surface by ion bombardment), etc., and that it is therefore only an order of magnitude which applies to the most current alloys and modes of deposition. In certain cases, decohesions between 0.03 and 0.1 mm could also give rise to emission of solid or liquid particles, even in the absence of large dissolved or occluded hydrogen contents (>0.2 ppm).

In order to prevent unnecessary transformation of precursors originally containing redhibitory decohesions, which particularly allows one to reduce the level of rejection during testing, a variant of the process according to the invention includes a test of the precursors and/or of the intermediate products, allowing one to determine their internal soundness, that is, to determine the size of the decohesions which they contain, as well as the number of decohesions per unit of volume.

In particular, these tests are advantageously performed on slices of rough cast billet adjacent to the part intended for transformation into the target. These tests are preferably performed on the flat surfaces of the slices. During these tests, one preferably selects the precursors and/or intermediate products which have no decohesion larger than 0.1 mm and less than 10 decohesion larger than 0.04 mm per slice.

The tests on billet slices are advantageously performed after a homogenization heat treatment, which makes it possible to avoid confusing the decohesions and the intermetallic phases precipitated during solidification.

It is also advantageous to perform the internal soundness tests on the intermediate products coming from a first step of working of the billet slices, which tends to increase the size of the decohesions so as to make them redhibitory. The working is generally obtained by pressing, forging or rolling. These intermediate tests allow one to avoid unnecessarily continuing the transformation to the final manufacturing step of the target. During these tests, one preferably selects the precursors and/or intermediate products which have no decohesion larger than 0.1 mm and less than 10 decohesions larger than 0.04 mm per piece.

The cathode sputtering target precursors, made of very pure aluminum or of very pure aluminum alloy, for the metallization of integrated circuits or of electronic circuits, therefore preferably contain less than 10 decohesions larger than 0.04 mm per 100 cm$^3$.

The implementation of the invention will be better understood from the detailed examples hereafter.

EXAMPLES

The preferred embodiment of the process according to the invention is applied here to an aluminum alloy containing 1% silicon and 0.5% copper for a target, but it is obviously not limited to this aluminum alloy alone.

Preparation of the targets

From thirteen different casting operations of the same Al+1% Si+0.5% Cu alloy, the applicant removed a section of the crude billet, with a unit length of 600 mm and a crude diameter of 137 mm. The hydrogen content of these cast products was systematically less than 0.20 ppm and generally less than 0.10 ppm as measured with an Alscan® brand apparatus, based on liquid metal in the casting, and confirmed by measurement using a Stroehlein® brand apparatus for extraction of the gas by melting under a vacuum based on solid samples removed from slices of billets adjacent to the sampled section.

Using these slices adjacent to the 600-mm-long pieces, a test was also conducted for measuring the inclusion content, consisting of dissolving the aluminum alloy matrix and collecting by filtration the insoluble nonmetallic inclusions (filtering threshold $\geq 2 \mu m$), which after drying, are weighed and then counted and measured by scanning microscopy.

The thirteen sections of billets were, in a first step, descaled on a lathe in order to eliminate the surface casting skin, and their diameter was brought to 130 mm. Then, these sections of billets thus descaled were subjected to a conventional ultrasonic inspection at a frequency of 5 MHz, so as to only use the sections with no echo greater than that of an artificial defect represented by a flat bottom [hole] with a diameter of 0.7 mm, according to the French standard AIR No. 9051, which is the most severe standard existing for this type of rough cast product. This led to the rejection of one section.

The sensitivity of this test adjusted to this level of frequency by the choice of an ultrasound sensor and a conventional measurement sequence allows one to detect equivalent defects between 0.3 and 0.8 mm. One will preferably use the standard AIR 9051 in its variant called the helical test, which allows one to inspect 100% of the volume of the billet because the sensor is given a translational movement at right angles with the billet which is itself given a rotational movement, whereas the basic test according to the standard inspects only the surfaces and the three generatrices of the billet.

This led to the rejection of one section which furthermore allowed one to observe that the inclusion content measured on one of the slices adjacent to this section exceeded 10 mg of inclusions with a size greater than 2 $\mu m$/kg of metal, whereas this content remained lower than 5 mg of inclusions with a size greater than 2 $\mu m$/kg of metal on all the slices adjacent to the twelve sections which satisfied the requirements of this first ultrasound test.

The twelve sections thus selected were then transformed into target blanks, according to the mode of operation described in EP-A-0,466,617 (U.S. Pat. No. 5,160,388) attributed to the applicant, except that the homogenization treatment was slightly adapted for this alloy in particular.

This homogenization was done in two stages, the first stage corresponding to maintaining 510° C. for 8 h, so as to put the constituents of the ternary eutectic appearing at the end of solidification back in solution, followed by a second stage consisting of maintaining 560° C. for another 4 h, in order to perfect the homogeneity of chemical composition of the product, on the scale of the individual grains. After sectioning each billet approximately 600 mm thick into three pieces 160 mm wide separated by control sections, the rest of the operations were carried out entirely according to the instruction of the aforementioned patent and led to target blanks with a diameter of approximately 330 mm and a thickness of 25 mm, after working operations including pressing, cross rolling and a final recrystallization heat treatment at a rate of three targets per piece with an initial length of 600 mm.

One surface of each blank was then machined and polished so as to examine the micrographic structure of the transformed products. This examination revealed that the products contained fine precipitates of silicon and intermetallic $Al_2Cu$, whose average size was close to 5 to 10 $\mu m$, and that the grain size of these recrystallized products was less than 0.1 mm and, on average, on the order of 0.07 mm. Furthermore, the texture of these targets, as revealed by an X-ray examination (pole figures 111 and 200), was very perceptibly isotropic, without preferential orientations of the grains.

All the blanks thus produced therefore corresponded, for all these criteria (size of the precipitates, grain size, texture of orientation of the grains), to all the criteria expected for satisfactory use of the targets for metallization of integrated circuits.

These blanks therefore underwent final machining on a lathe to obtain disks with a diameter of 300 mm and a thickness of 20 mm, with a unit weight of approximately 3.8 kg, and a volume close to 1400 $cm^3$. The ultrasonic inspection conducted manually by moving the sensor parallel to the surface of the target with a sensor/target contact produced by a mineral grease, at a frequency of 5 MHz, allowed one to eliminate the disks with defects equivalent to the artificial defect consisting of a flat-bottomed hole of 0.7 mm, according to the French standard AIR No. 9051. This standard used preferably for rough cast products can be advantageously replaced by standards more frequently used for transformed products, such as AECMA-Pr EN 2003-8 and Pr EN 2004-2 or else MIL STD 2154 and Pr EN 4050-4. Six blanks out of thirty-six were thus rejected in this test.

Selection after high-frequency ultrasonic inspection

Before connecting the remaining disks by welding to their copper support plate, they underwent an additional test using high-frequency ultrasound.

This additional test consisted of immersing each machined disk in a tank of water. Then, an ultrasound sensor or probe operating at a frequency of 15 MHz was moved parallel to the surface of the disk according to an X-Y scanning. This sensor was previously calibrated with respect to artificial defects consisting of flat-bottomed holes with a diameter of 0.1 mm, located at depths of 6 mm, 12 mm and 18 mm under the surface of an identical alloy with metallurgical characteristics similar to those of the product to be tested. It should be noted on this subject that this standard plate, which itself had an average grain size of 0.07 mm, an isotropic orientation of the grains, and small intermetallic precipitates (on the average less than 10 $\mu m$), allows as well for a standardization of the sizes of defects on other aluminum alloys with small loads with identical morphological characteristics.

This made it possible to plot the standardization curve giving the measurement of the amplitude of the echo corresponding to an equivalent flat-bottomed hole.

For each disk, the number of echoes exceeding the noise level and the amplitude of the associated signal were counted, in the maximum active volume, as was the number of echoes exceeding the amplitude corresponding to the artificial defect of 0.1 mm, that is, a volume of approximately 1000 $cm^3$ corresponding to an active surface with a diameter of 280 mm, over a depth of 18 mm below the surface.

The disks thus tested were separated into five categories;

Category 1: Disks with more than 1000 echoes >0.1 mm per disk (more than 1 echo/cm$^3$)

Category 2: Disks with 100 to 1000 echoes >0.1 mm per disk (0.1–1 echo/cm$^3$).

Category 3: Disks with 10 to 100 echoes >0.1 mm per disk (0.01–0.1 echo/cm$^3$).

Category 4: Disks with fewer than 10 echoes >0.1 mm per disk (less than 0.01 echo/cM$^3$).

Category 5: Disks having only indications between 0.03 and 0.1 mm none of which is greater than 0.1 mm per disk.

The disks of these five categories, all in accordance with the selection criteria existing for sputtering targets, concerning the grain size, the orientation texture, the size of the precipitates, and the absence of defects larger than 0.7 mm, were then connected by welding them to their copper supports.

One then obtained:

Three targets of Category 1 (more than 1 echo/cm$^3$ of active metal)

Ten targets of Category 2 (0.1–1 echo/cm$^3$ of active metal)

Twelve targets of Category 3 (0.01–0.1 echo/cm$^3$ of active metal)

Five targets of Category 4 or 5 (less than 0.01 echo/cm$^3$ of active metal).

These targets were than used by a manufacturer of integrated circuits for the metallization of 8-in diameter substrates for manufacturing 16 MB DRAM memories.

Results of the comparative metallization tests

Of the three targets of Category 1, two had to be stopped very quickly, with extremely frequent appearance of microarcs and abundant deposition of particles on the substrates, leading to 100% rejection of these substrates. The third target was used until the normal end of its lifetime, but with mediocre results: more than 20% of the substrates metallized with this target had to be rejected because of the excessive presence of particles larger than 0.5 µm.

Of the ten targets of Category 2, two had to be stopped before the normal end of their lifetime, because of the very frequent appearance of microarcs and abundant deposits of particles on the substrates. The other eight gave mediocre results, on the average more than 10% of the substrates rejected after metallization.

With regard to the twelve targets of Category 3, none had to be stopped during use, and on average, less than 5% of the metallized substrates had to be rejected because of abundant presence of particles.

Finally, with regard to the five targets of Categories 4 and 5, none gave rise to problems, and the proportion of metallized substrates which had to be rejected because of the abundant presence of particles was on the average less than 2%.

It was possible to note also that the measurements of inclusion content made on slices adjacent to the pieces from which the targets of Categories 3, 4, and 5 came showed a weight content of less than 5 mg of inclusions per kilogram of metal for all these targets. On the other hand, several of the targets, of the preceding Categories 1 and 2, obtained also from such pieces, and therefore with similar inclusion contents, provided confirmation that a low inclusion content was without doubt a necessary but not, in any case, a sufficient condition for obtaining a low level of redeposition of the particles.

Before the destructive measurements of hydrogen content and inclusions, using the billet slices adjacent to the sections transformed into targets, high frequency ultrasonic tests were performed, with a focused beam, under conditions similar to the tests performed on the targets. These tests showed that the targets which gave rise to numerous defects during cathode sputtering came from billet sections of which at least one adjacent slice already contained several decohesions larger than 0.1 mm, whereas the targets which gave rise to the least number of defects came from pieces whose adjacent slices contained few decohesions larger than 0.04 mm, that is, less than 10 decohesions per slice.

Targets were produced under conditions comparable to those described above, but starting exclusively with pieces whose adjacent slices had less than 6 decohesions larger than 0.04 mm per slice. The inspected volume being 60 cm$^3$, with a diameter of 125 mm and an inspected thickness of 5 mm, the number of decohesions larger than 0.04 mm is less than 10 per 100 cm$^3$. The products obtained were characterized after homogenization and reduction of thickness to a value equal to twice the thickness of the final target, which showed that less than 5% of these intermediate products had a number of large decohesions, that is, greater than 0.1 mm, greater than one per 100 cm$^3$. The final targets obtained after reduction of the thickness to the final value and after machining were more than 90% free of decohesions larger than 0.1 mm and contained less than 30 decohesions larger than 0.04 mm per 100 cm$^3$. The results obtained during the depositions by cathode sputtering with targets free of decohesions larger than 0.1 mm and containing less than 10 decohesions larger than 0.04 mm per cm$^3$ were excellent. Those obtained with targets free of decohesions larger than 0.1 mm but containing more than 10 decohesions larger than 0.04 mm per 100 cm$^3$ were considerably less satisfactory.

Other application examples

A) Aluminum alloy containing 1% silicon

Using existing lots of cathode sputtering targets coming from different casting operations and produced out of the same aluminum alloy with a very high degree of purity, greater than 99.999%, containing additions of 1 wt % silicon, one performed a highfrequency (15 MHz) ultrasonic inspection by immersion, and one selected:

on the one hand, a first lot of five targets containing less than 0.1 decohesion with an equivalent size greater than 0.1 mm per cubic centimeter of metal, and no defect larger than 0.7 mm on the other hand, a second lot of five targets containing more than 2 decohesions with an equivalent size greater than 0.1 mm per cubic centimeter of metal, without any of these defects exceeding an equivalent size greater than 0.7 mm.

The targets thus selected as a function of their density of defects between 0.1 and 0.7 mm were used on an experimental basis, alternately, in the same cathode sputtering machine, for metallizing a series of semiconductor substrates with a diameter of 6 in (approximately 150 mm), with a thickness of the deposited aluminum of 1 µm. Each target was then used to metallize several tens of consecutive substrates.

These substrates were then sorted on the basis of the criteria used for etching integrated circuits of the 16 MB DRAM memory, with an etching fineness of 0.35 µm.

It was then observed that more than 95% of the substrates metallized from targets with a very low density of decohesions larger than 0.1 mm were judged suitable for this application according to these criteria concerning the presence or absence of deposited particles.

In contrast, more than 20% of the substrates metallized form targets with a high density of decohesions larger than 0.1 mm but smaller than 0.7 mm were judged unacceptable for this application, according to the same criteria.

B) Aluminum alloys containing 0.5% copper

After use in an apparatus for metallization of semiconductor substrates with a high integration density, targets were selected, which were partially used (depth of erosion on the order of 5 mm) made of a binary Al+0.5% Cu alloy, which gave rise to high levels of redeposition of solid or liquid particles on the substrates thus metallized, these high levels of redeposition having led to rejection of more than 10% of these substrates.

These partially used targets, in a first step, were separated from their copper support plates and then remachined dry (with no machining lubricant) with a diamond tool, in order to eliminate their surfaces which were possibly oxidized or contaminated.

These targets thus remachined were then subjected to an ultrasonic examination, first over a wide frequency band of 10–25 MHz, centered at 15 MHz, and allowing one to detect and count the defects with a diameter greater than or equal to 0.4 times that of a standard flat-bottomed hole with a diameter of 0.1 mm.

It was then observed that all these targets thus remachined, coming from defective targets, contained a defect density greater than one defect of equivalent size greater than 0.04 mm per cubic centimeter of metal inspected.

In contrast, for this alloy with a low solidification interval, curiously, only two of the four targets contained more than 0.05 defects with an equivalent size greater than 0.1 mm per cubic centimeter of metal inspected.

Each target thus inspected was then diametrically resawed to obtain two semicircular half-targets.

One half-disk per target was then subjected to a dissolution test, for the purpose of dissolving the aluminum alloy matrix and quantifying the initial content of the initial target in terms of insoluble refractory inclusions.

It was thus observed that all the defective targets subjected to this test contained more than 5 mg of refractory inclusions per kilogram of alloy.

The other half-disk coming from each target was machined in such a way as to extract from it a solid cylindrical sample for measuring the contents of these samples in terms of dissolved or occluded hydrogen, using a Stroehlein® apparatus. It was thus observed that the hydrogen content of the metal coming form the defective targets was greater than 0.12 ppm.

For the sake of comparison, after a sputtering test of limited duration (approximately 25% of their normal lifetime), four metallization targets were removed, which, during this test of significant but limited duration, gave a very low level of rejection due to redeposition of solid or liquid particles (less than 1% rejection).

These partially used targets were subjected to the same examinations as those corresponding to the defective targets. It was thus observed that these targets of excellent quality systematically had refractory inclusion contents of less than 4 mg per kg of metal and dissolved or occluded hydrogen contents of less than 0.07 ppm. None of these targets had any internal decohesions larger than 0.1 mm, and they had less than 0.05 decohesion larger than 0.04 mm per cubic centimeter of metal thus examined; which was considerably lower than what was observed using the "defective" targets.

C) Nonalloyed aluminum with a purity of 4 N to 6 N

As a nonlimiting example, of the existing lots of cathode sputtering targets coming from rolling using a crude casting blank with a rectangular section of aluminum with a purity greater than 99.998%, one selected after 15-MHz ultrasonic inspection:

on the one hand, a first lot of five rectangular targets containing less than 0.01 decohesion with an equivalent size greater than 0.1 mm per cubic centimeter of metal, and no defect larger than 0.7 mm on the other hand, a second lot of five targets containing more than 0.5 decohesion with equivalent size greater than 0.1 mm per cubic centimeter of metal, with none of these defects exceeding an equivalent size of greater than 0.7 mm.

The targets thus selected as a function of their defect density with size between 0.1 mm and 0.7 mm were used experimentally, alternating in a cathode sputtering machine, in order to metallize a series of 500 rectangular substrates, intended for the production of liquid-crystal displays with dimensions of approximately 21×28 cm (so-called "14-in" screens), with a thickness of deposited aluminum of 1 $\mu$m and an etching width of 10 $\mu$m (therefore much greater than that of the ultra-large-scale integrated circuits). Each target was used to metallize fifty consecutive substrates. These substrates were then sorted as function of the criteria ordinarily used for the etching of these rather large screens, in which any local etching defect leads to the rejection of the entire metallized substrate.

It was then observed that more than 95% of the substrates metallized using targets with a very low density of decohesions larger than 0.1 mm were judged suitable for this application according to these criteria concerning the presence or absence of deposited particles.

In contrast, more than 15% of the substrates metallized using targets with a high density of decohesions larger than 0.1 mm, but smaller than 0.7 mm, were judged unacceptable for this application, according to these same criteria.

Value of the invention

These various application examples demonstrate the great economic value of the invention since, using cathode sputtering targets for the metallization of integrated circuits or electronic circuits, selected in a suitable manner by a method which does not destroy said targets, it is possible to reduce the level of rejection of the metallized substrates due to redeposition of solid or liquid particles to less than 5%.

We claim:

1. A process for testing cathode sputtering targets, which can be used for metallization of integrated circuits or electronic circuits and which include an active part made of aluminum with a very high degree of purity or of a very pure aluminum alloy, the process comprising:

determining a size of decohesions of the targets to be tested, performing a count in terms of size and number of internal decohesions per unit volume of said targets to be tested, and selecting, according to a criterion based on a distribution of the decohesions in terms of size and number, selected targets that allow one to reduce a level of rejection of metallized substrates, because of redeposition of solid or liquid particles, to less than 5%, wherein said process is non-destructive to said targets to be tested.

2. The process according to claim 1, characterized by the fact that the size of the decohesions of the targets to be tested is determined by comparison with reference targets or with artificial reference defects.

3. The process according to claim 2, characterized by the fact that the selected targets have a decohesion density less than or equal to 0.1 decohesion larger than 0.1 mm per cubic centimeter of active metal of the selected targets.

4. The process according to one of claims 1 and 2, characterized by the fact that the selected targets have a decohesion density less than 0.01 decohesion larger than 0.1 mm per cubic centimeter of active metal of the selected targets.

5. The process according to claim 1, characterized by the fact that the selected targets have a decohesion density less than or equal to 0.1 decohesion larger than 0.1 mm per cubic centimeter of active metal of the selected targets.

6. The process according to claim 1, characterized by the fact that the size of the decohesions is determined using ultrasound.

7. The process according to claim 6, comprising:

providing an ultrasonic sensor functioning at an operating frequency greater than 5 MHZ, adjusting a measurement sequence to indicate an amplitude of an ultrasound echo of an artificial defect of known size, simulating a decohesion in a target immersed in a liquid as a function of a position of said defect with respect to a surface of the target, determining the size of the decohesions of the targets to be tested by comparison with the amplitude of the ultrasound echo obtained with the artificial defect in a given volume parameterized by the ultrasonic inspection, performing a count in terms of size and number of internal decohesions per unit volume of said targets to be tested, and selecting, for applications requiring a very high degree of etching fineness, selected targets having a decohesion density less than or equal to 0.1 decohesion larger than 0.1 mm per cubic centimeter of active metal of the selected targets.

8. The process according to claim 7, characterized by the fact that the ultrasound sensor functions at an operating frequency between 10 and 25 MHz, and the selected targets have no internal decohesions larger than 0.1 mm and less than 0.1 decohesion larger than 0.04 mm per cubic centimeter of active metal of the selected targets.

9. The process according to claim 8, characterized by the fact that the selected targets have no internal decohesion larger than 0.1 mm and less than 0.05 decohesion larger than 0.04 mm per cubic centimeter of active metal of the selected targets.

10. The process according to claim 7, wherein said ultrasonic sensor functions at an operating frequency between 10 and 50 MHz.

11. The process according to claim 7, characterized by the fact that the selected targets have a decohesion density less than 0.01 decohesion larger than 0.1 mm per cubic centimeter of active metal of the selected targets.

12. The process according to claim 7, characterized by the fact that the ultrasound sensor functions at an operating frequency centered at 15 MHz, and the selected targets have no internal decohesions larger than 0.1 mm and less than 0.1 decohesion larger than 0.04 mm per cubic centimeter of active metal of the selected targets.

13. The process according to claim 1, characterized by the fact that the size of the decohesions is determined using X-rays.

14. The process according to claim 1, characterized by the fact that the size of the decohesions is determined using eddy currents.

15. The process according to claim 1, wherein said sputtering targets are made from precursors of the cathode sputtering targets comprising aluminum with a very high degree of purity or a very pure aluminum alloy, wherein said precursors have less than 10 decohesions larger than 0.04 mm per 100 cm$^3$.

16. The process according to claim 1, wherein said sputtering targets are made from precursors selected by a method for testing internal soundness of metal, said method not being destructive and being sensitive to internal decohesions.

17. The process according to claim 1, wherein said sputtering targets are made from intermediate products selected by a method for testing internal soundness of metal, said method not being destructive and being sensitive to internal decohesions.

* * * * *